United States Patent [19]

Lien

[11] 4,237,169

[45] Dec. 2, 1980

[54] INHIBITION OF PROLACTIN RELEASE BY AN AMINOBENZYLCYCLOALKANOL

[75] Inventor: Eric L. Lien, Paoli, Pa.

[73] Assignee: American Home Products Corporation, New York, N.Y.

[21] Appl. No.: 60,257

[22] Filed: Jul. 25, 1979

[51] Int. Cl.³ .......................................... A61K 31/135
[52] U.S. Cl. .................................................... 424/330
[58] Field of Search ......................................... 424/330

[56] References Cited

U.S. PATENT DOCUMENTS

| 3,928,626 | 12/1975 | Yardley et al. | 424/330 |
| 4,017,637 | 4/1977 | Yardley et al. | 424/330 |
| 4,155,935 | 5/1979 | Yardley | 424/248.57 |

*Primary Examiner*—Douglas W. Robinson
*Attorney, Agent, or Firm*—George Tarnowski

[57] ABSTRACT

Administration of the compound 1-cis-2-(α-dimethylamino-m-hydroxybenzyl)cyclohexanol inhibits release of prolactin.

1 Claim, No Drawings

INHIBITION OF PROLACTIN RELEASE BY AN AMINOBENZYLCYCLOALKANOL

This invention relates to the chemical compound 1-cis-2-(α-dimethylamino-m-hydroxybenzyl)cyclohexanol and its use in the inhibition of prolactin release in the treatment of conditions requiring the regulation of the release of this hormone.

Prolactin is an important pituitary hormone whose physiological functions include the promotion of mammary gland development and the induction of lactation. Prolactin secretion is regulated by the thyrotropin releasing factor (thyroliberin or TRH) and dopamine which are secreted by the hypothalamus. It is known that the administration of various substances will stimulate prolactin release: for example, the narcotic-analgesic morphine, the endogenous brain analgesic peptide methionine-enkephalin, and certain methionine-enkephalin analogs, have been demonstrated to effect release of prolactin. It is also known that certain substances will inhibit prolactin release:for example, the narcotic antagonist nalaxone inhibits prolactin release [see C. Shaar et al., Fed. Proc., 36, 311 (1977)] and the opiate antagonist described in U.S. Pat. No. 4,143,158. Inhibition of prolactin release is useful in the treatment of those conditions where excessive prolactin levels are undesirable, as for example in the treatment of galactorrhea and infertility due to hyperprolactinemia.

The invention is directed to a method for inhibiting prolactin release in warm-blooded animals which comprises administering to such a warm-blooded animal an effective amount of 1-cis-2-(α-dimethylamino-m-hydroxybenzyl)cyclohexanol, or a pharmacologically acceptable acid addition salt thereof.

The compound employed in the method of this invention is an analgesic. This compound, its method of preparation and its method of use as an analgesic are described in U.S. Pat. Nos. 3,928,626; 4,017,637; and 4,155,935.

In carrying out the method of this invention the active compound can be administered either alone or in combination with inert pharmaceutically acceptable carriers in a variety of dosage forms, orally or parenterally. The dose requirements will vary with the severity of the conditions being presented, the animal being treated, or the dosage form employed. Therapy is instituted at low dosages and the dosage is increased incrementally until the desired prolactin-inhibiting effect is achieved.

Prolactin in blood samples can be determined by the specific double antibody radioimmunoassay method of Neill and Reichert, Endocrinology, 88, 548 (1971).

With large animals (about 70 kg. body weight), by the parenteral route, such as by intramuscular or subcutaneous injection, an effective dose is from about 1 mg. to about 100 mg., preferably about 5 mg. to about 20 mg.

For unit dosages, the active compound can be compounded into any of the usual oral or parenteral dosage forms, including tablets, capsules, elixir, or suspensions. The dosage forms can contain conventional inert pharmaceutical carriers as diluents, lubricating agents, stabilizing agents, preserving agents, or flavoring agents, as needed. Suitable pharmaceutical carrying agents and methods of preparation thereof will be apparent to those skilled in the art. In all cases, the proportions of the active ingredient in a dosage form must be sufficient to impart prolactin inhibiting activity thereto.

The ability of 1-cis-2-(α-dimethylamino-m-hydroxybenzyl)-cyclohexanol to inhibit prolactin release has been demonstrated in rats as described in the following Example:

EXAMPLE

Male Charles River CD rats (300–350 g.) are given a subcutaneous injection of 1-cis-2-(α-dimethylamino-m-hydroxybenzyl)cyclohexanol in saline or of saline alone (controls). At the specified times the animals are decapitated and blood is collected in Traysylol-EDTA (12 mg. EDTA in 6000 units Traysylol). Each plasma sample is assayed for prolactin in triplicate by specific double antibody radioimmunoassay using NIAMDD reagents. Prolactin is determined by the method of Neill and Reichert, Endocrinology, 84, 548 (1971). The results are shown in the table below:

| Treatment | Dose (mg/kg) | Time to Blood Sampling (min.) | Prolactin (ng/ml) |
|---|---|---|---|
| Saline | — | 30 | 16 ± 2 |
| Compound | 2 | 30 | 5 ± 1* |
| Saline | — | 120 | 35 ± 6 |
| Compound | 2 | 120 | 16 ± 3* |
| Saline | — | 240 | 44 ± 8 |
| Compound | 2 | 240 | 17 ± 3* |
| Water | — | 120 | 42 ± 10 |
| Compound① | 5 | 120 | 12 ± 2* |

*= p<0.01;
① = administered perorally

The results show that 1-cis-2-(α-dimethylamino-m-hydroxybenzyl)cyclohexanol significantly lowers serum prolactin levels in normal male rats.

What is claimed is:

1. A method for lowering blood serum prolactin levels in warm-blooded animals which comprises administering to a warm-blooded animal in need of a lowered serum prolactin level an amount of 1-cis-2-(α-dimethylamino-m-hydroxybenzyl)-cyclohexanol, or a pharmacologically acceptable acid addition salt thereof, effective to bring about said lowering of the serum prolactin level.

* * * * *